United States Patent [19]

Szczepanski et al.

[11] 3,959,392
[45] May 25, 1976

[54] PROCESS FOR PREPARING CHLOROHYDROQUINONE

[75] Inventors: Norbert Szczepanski; Konrad Baessler, both of Frankfurt am Main, Germany

[73] Assignee: Hoechst Aktiengesellschaft, Frankfurt am Main, Germany

[22] Filed: Nov. 19, 1974

[21] Appl. No.: 525,182

[30] Foreign Application Priority Data
Nov. 24, 1973 Germany............................ 2358623

[52] U.S. Cl........................... 260/621 H; 260/623 R
[51] Int. Cl.$^2$................... C07C 39/08; C07C 39/28
[58] Field of Search........ 260/623 R, 623 H, 621 R, 260/621 H

[56] References Cited
UNITED STATES PATENTS 1,912,744 6/1933 Bramer et al. .................. 260/623 R
2,748,173 5/1966 Rodgen ........................... 260/623 R

OTHER PUBLICATIONS

Roberts et al., "Basic Principles of Organic Chem.", 1965.
Grinev et al., "Chem. Abs.", Vol. 49 (1955), p. 12353c.

Primary Examiner—James O. Thomas, Jr.
Assistant Examiner—W. B. Lone
Attorney, Agent, or Firm—Connolly and Hutz

[57] ABSTRACT

Preparation of chlorohydroquinone by adding hydrogen chloride to p-benzoquinone, wherein a 1 to 20 % by weight solution of p-benzoquinone in benzene is treated discontinuously or continuously with hydrogen chloride at a hydrogen chloride pressure of from 1 to 6 atmospheres gauge, at a temperature of from 40° to 80°C, the residence time being from 1 to 4 hours and the chlorohydroquinone is isolated in known manner.

9 Claims, No Drawings

PROCESS FOR PREPARING CHLOROHYDROQUINONE

The present invention relates to a process for preparing chlorohydroquinone by adding hydrogen chloride to p-benzoquinone at elevated pressure and temperatures using benzene as solvent.

Chlorohydroquinone is a known intermediate for many organic chemicals and is used, inter alia, for syntheses of chlorohydroquinone dialkyl ethers which are important primary products for dyestuffs.

Two ways for preparing chlorohydroquinone are known from literature: the chlorination of hydroquinone with elementary chlorine in aqueous glacial acetic acid or in carbon tetrachloride or the addition of hydrogen chloride to p-benzoquinone.

The process using aqueous glacial acetic acid (U.S. Pat. No. 2,748,173) has the disadvantage that considerable quantities of higher chlorinated products are obtained besides unreacted hydroquinone, whereas the preparation of the monochloro compound by chlorination in carbon tetrachloride (U.S. Pat. No. 1,912,744 requires a high technical expenditure for distilling, thus rendering the process uneconomic.

These inconveniences are avoided in the direct conversion of p-benzoquinone into chlorohydroquinone by adding hydrogen chloride.

The use of a polar solvent, for example, chloroform or, as it is known from more recent literature, of diethyl ether or dioxane (C.A. 49, page 12, 353 (1954)) is typical for this method known for a long time (Ann. 210, page 138 (1881)). Because of the easy decomposability of p-benzoquinone temperatures of about 0°C are recommended for the reactions hitherto carried out only batchwise.

Recently, processes for preparing p-benzoquinone by anodic oxidation of benzene have become more and more important. The benzenic p-benzoquinone solutions prepared according to German Offenlegungsschriften Nos. 2,108,623 and 2,221,691 contain from 2 to 8 % by weight of benzoquinone. They may be further concentrated by carefully distilling them, but the isolation of benzoquinone is complicated and causes great losses because of its easy decomposability.

It was therefore desirable to effect the addition of hydrogen chloride directly in benzene, preferably after concentrating the p-benzoquinone to 10 to 15 % by weight. If the method known from literature is transferred to the addition of hydrogen chloride in benzene as solvent, useful reaction products are only obtained after a reaction time of 15 hours. When the addition of hydrogen chloride is brought about in the desired continuous process in a cascade consisting of four stirring apparatus, an adequate quality of the hydroquinone is only obtained after an average residence time of more than 12 hours. In the case of shorter reaction times the conversion obtained is uncomplete despite of a sufficient hydrogen chloride supply, which can be seen from the greenish black addition products of chlorohydroquinone and p-benzoquinone. The long reaction times in benzene result from the fact that the solvent is unpolar and from the low solubility of the intermediate quinhydrone and of the hydrogen chloride in benzene. An economic preparation of chlorohydroquinone, consequently, is not possible.

It has now be found that hydrogen chloride can be added to p-benzoquinone advantageously and especially economically, in benzene as solvent, as well in a batch process as in a continuous process, by operating at a hydrogen chloride pressure of from 1 to 6 atmospheres gauge, preferably 3 to 4 atmospheres gauge and a temperature of from 40° to 80°C preferably from 60° to 70°C. It is surprising and unexpected with regard to the easy decomposability of the p-benzoquinone that the reaction not only takes place quantitatively but that the chlorohydroquinone formed is also obtained in a purity of more than 90 %.

By carrying out the reaction according to the invention under incresed hydrogen chloride pressure, preferably 3 to 4 atmospheres gauge, and at a temperature of from 60° to 70°C the reaction time is reduced to 2 to 3 hours. This signifies that the quantity passed per unit of time through the cascade apparatus composed of 4 agitator vessels is five times higher than the quantity passed through at atmospheric pressure so that the technical preparation of chlorohydroquinone by the process according to the invention may be realised continuously in an especially advantageous manner. Moreover, as compared to the known hydrogen chloride addition at atmospheric pressure a cascade consisting of 2 agitator vessels only is required.

The process according to the invention is carried out advantageously in agitator vessels, being optionally connected in cascade form, for example up to five. Preferably used are cascades consisting of from 2 to 4, preferably of 2 agitator vessels. The process may also be carried out in one agitator vessel, provided that the required residence times can be maintained. Other devices may also be used, if the abovementioned reaction conditions can be realised and if the reactor material has the required chemical resistance against the reaction components. Preferably used corrosion-resistent materials are, for example, enamelled steel or stainless steel.

The reaction temperature should not be below 40°C, because, otherwise, when using from 10 to 15 % by weight benzenic p-benzoquinone solutions, the quality of the reaction product could be considerably diminished by admixed quinhydrones.

As a starting component for the process according to the invention up to 20 % by weight benzenic solutions of p-benzoquinone, preferably from 10 to 15 % by weight solutions, are generally used. Starting concentrations of more than 20 % by weight are also possible, but they may optionally require the addition of further amounts of solvent (benzene) before working up the reaction product, in order to liquify the reaction mixture solidified by cristallization.

After expansion of the reaction mixture and after neutralisation of still remaining hydrogen chloride with sodium carbonate benzene free from chloride may be obtained by simple and distillation and recycled to the electrochemical oxidation.

The chlorohydroquinone may also be obtained by countercurrent extraction with water besides the methode wherein it is isolated in the form of a solid matter.

The following examples illustrate the invention.

EXAMPLE 1

2700 g = 3000 ccm of a 12 % by weight benzenic p-benzoquinone solution were heated to 65°C while stirring in an enamelled 5 l autoclave with stirrer. Thereafter, hydrogen chloride was introduced under pressure by a valve until a pressure of 3.5 atmospheres gauge was obtained. This pressure was maintained for the test period of 2.5 hours. It could be noticed that hydrogen chloride was no longer consumed after about 2 hours. The reaction mixture was then cooled to room temperature, expanded and nitrogen was blown through for about 1 hour. Possibly remaining dissolved hydrogen chloride was eliminated by neutralising it with sodium carbonate.

After distilling off the benzene, 433 g of chlorohydroquinone of white aspect were obtained. The conversion, calculated on p-benzoquinone used was quantitatively, the melting point of the crude product was 100° – 101°C. The yield of chlorohydroquinone, calculated on p-benzoquinone used, was 91 % of the theory.

EXAMPLE 2

The apparatus consisted of two cascade connected enamelled agitator vessels provided with heating jackets and each having an effective capacity of 600 ccm. The overflow of the reaction mixture was assured by a dip pipe going to the bottom. The first vessel was provided with two feed valves, the second one with an expansion valve.

After heating to 63°C the 12 % by weight benzenic p-benzoquinone solution occupying about ⅓ of the effective volume a hydrogen chloride pressure of 3.5 atmospheres gauge was produced. 405 g = 450 ccm per hour of the 12 % by weight benzenic p-benzoquinone solution was introduced by pumping into the whirling liquid of the first vessel while maintaining the pressure. 419 g = 465 ccm per hour of the benzenic chlorohydroquinone solution were drawn off from the second agitator vessel (65°C) by the expansion valve and passed into a further stirring vessel, whereby the volume in both vessels remained constant. The hydrogen chloride obtained during the expansion was recycled by means of a compressor while replacing the consumed quantity (about 17 g per hour).

After neutralising the remaining hydrogen chloride with about 10 g per hour of anhydrous sodium carbonate 353 g per hour of benzene free from chloride and 65 g per hour of chlorohydroquinone could be isolated from the reaction solution by simple distillation. The crude product of white aspect had a melting point of from 100° to 101°C and consisted of:

4 to 5 % of hydroquinone
90 to 91 % of chlorohydroquinone
5 to 6 % of dichlorohydroquinone according to gaschromatographic analysis.

The same product quality during the whole test period of 100 hours was obtained, the conversion of p-benzoquinone being quantitative. The yield of chlorohydroquinone calculated on p-benzoquinone used was in the range of from 90 to 91 % of the theory.

What is claimed is:

1. Process for preparing chlorohydroquinone by adding hydrogen chloride to p-benzoquinone, which comprises treating a 1 to 20% by weight solution of p-benzoquinone in benzene with hydrogen chloride at a hydrogen chloride pressure of from 1 to 6 atmospheres gauge and a temperature of from 40° to 80°C, the residence time being of from 1 to 4 hours, and isolating the chlorohydroquinone.

2. Process as claimed in claim 1, which comprises using a 10 to 15 % by weight solution of p-benzoquinone in benzene.

3. Process as claimed in claim 1, wherein the reaction is carried out at a hydrogen chloride pressure of from 3 to 4 atmospheres gauge.

4. Process as claimed in claim 1, wherein the reaction is carried out at a temperature of from 60° to 70°C.

5. Process as claimed in claim 1, wherein the residence time is from 2 to 3 hours.

6. Process as claimed in claim 1, wherein the hydrogen chloride addition is effected continuously.

7. Process as claimed in claim 1, wherein the reaction is effected continuously in a cascade.

8. Process as claimed in claim 1, wherein p-benzoquinone obtained by electrochemical oxidation of benzene is used.

9. Process as claimed in claim 7, wherein the cascade consists essentially of 2 to 4 agitator vessels.

* * * * *